United States Patent [19]

Suzuki et al.

[11] Patent Number: 5,789,407

[45] Date of Patent: Aug. 4, 1998

[54] METHOD OF TREATING DEPRESSION WITH CERTAIN TRIAZINE DERIVATIVES

[75] Inventors: Fumio Suzuki, Mishima; Nobuaki Koike, Sunto-gun, both of Japan; Junichi Shimada, Belmont, Mass.; Shigeto Kitamura, Machida, Japan; Shunji Ichikawa; Joji Nakamura, both of Sunto-gun, Japan; Shizuo Shiozaki, Fuji, Japan

[73] Assignee: Kyowa Hakko Kogyo Co., Ltd., Tokyo, Japan

[21] Appl. No.: 424,397

[22] PCT Filed: Sep. 2, 1994

[86] PCT No.: PCT/JP94/01455

§ 371 Date: Apr. 25, 1995

§ 102(e) Date: Apr. 25, 1995

[87] PCT Pub. No.: WO95/07282

PCT Pub. Date: Mar. 16, 1995

[30] Foreign Application Priority Data

Sep. 6, 1993 [JP] Japan .................. 5-221431

[51] Int. Cl.⁶ ........................... A61K 31/535
[52] U.S. Cl. ............ 514/246; 514/233.2; 514/234.2; 514/234.5
[58] Field of Search ............... 514/246, 233.1, 514/233.2, 234.5

[56] References Cited

U.S. PATENT DOCUMENTS 4,780,464  10/1988  Trivedi .................. 514/250
5,356,894  10/1994  Rodney et al. ........... 514/233.2

FOREIGN PATENT DOCUMENTS 0379979  8/1990  European Pat. Off.
0552712  7/1993  European Pat. Off.

OTHER PUBLICATIONS

Pharmacol. Biochem. Behav., 16 (1982) 449.
Drug Dev. Res., 29 (1983) 38–55.
Chemical Abstracts AN 1990:191746, Nikodijevic et al., 1990.
Griebel et al, Psychopharmacology, 103(4) 541–4, Nov. 9, 1990.
Medline Abstract AN 86066118, Marenyo et al. Sep. 1995.

*Primary Examiner*—Keith D. MacMillan
*Attorney, Agent, or Firm*—Fitzpatrick, Cella, Harper & Scinto

[57] ABSTRACT

The present invention relates to an antidepressant containing as an active ingredient a triazine derivative or a pharmaceutically acceptable salt thereof, the derivative being represented by the following Formula (I):

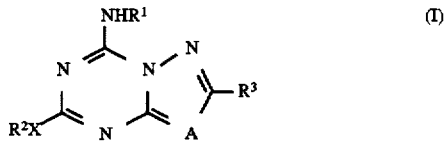

in which, $R^1$ represents hydrogen, substituted or unsubstituted lower alkyl, or substituted or unsubstituted lower alkanoyl; $R^2$ represents hydrogen, substituted or unsubstituted lower alkyl, substituted or unsubstituted lower alkenyl, substituted or unsubstituted cycloalkyl, substituted or unsubstituted aryl, substituted or unsubstituted aralkyl, or a substituted or unsubstituted heterocyclic group; $R^3$ represents a substituted or unsubstituted heterocyclic group; X represents a single bond, O, S, S(O), S(O)$_2$, or NR$^4$ (in which R$^4$ represents hydrogen, or substituted or unsubstituted lower alkyl; or $R^2$ and NR$^4$ are combined to form a substituted or unsubstituted 4 to 6-membered saturated heterocyclic group); and A represents N or CR$^5$ (in which R$^5$ represents hydrogen, or substituted or unsubstituted lower alkyl).

1 Claim, No Drawings

METHOD OF TREATING DEPRESSION WITH CERTAIN TRIAZINE DERIVATIVES

TECHNICAL FIELD

The present invention relates to an antidepressant.

BACKGROUND ART

It is known that compounds represented by the following formula (II):

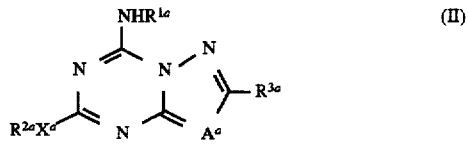

in which $R^{1a}$ represents hydrogen, substituted or unsubstituted lower alkyl, or lower alkanoyl, $R^{2a}$ represents hydrogen, lower alkenyl, substituted or unsubstituted cycloalkyl, substituted or unsubstituted phenyl, substituted or unsubstituted aralkyl, or a substituted or unsubstituted heterocyclic group, $R^{3a}$ represents a substituted or unsubstituted 5-membered heterocyclic group, $X^a$ represents O, S, S(O), S(O)$_2$, or $NR^{4a}$ (in which $R^{4a}$ represents hydrogen, or substituted or unsubstituted lower alkyl, or $R^{2a}$ and $NR^{4a}$ are combined to form a substituted or unsubstituted 4 to 6-membered saturated heterocyclic group), and $A^a$ represents N or $CR^{5a}$ (in which $R^{5a}$ represents hydrogen, or substituted or unsubstituted lower alkyl), and compounds represented by the following formula (III):

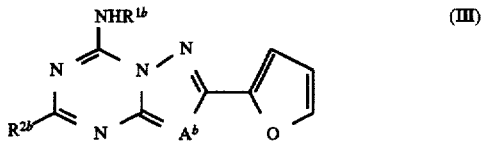

in which $R^{1b}$ represents hydrogen, substituted or unsubstituted lower alkyl, or lower alkanoyl, $R^{2b}$ represents substituted or unsubstituted lower alkyl, lower alkenyl, lower alkynyl, substituted or unsubstituted phenyl, or a substituted or unsubstituted 5- or 6-membered heterocyclic group, and $A^b$ represents N or $CR^{5b}$ (in which $R^{5b}$ represents hydrogen, or substituted or unsubstituted lower alkyl), have an selective adenosine A$_2$ antagonistic activity (Japanese Published Unexamined Patent Application Nos. 97855/93 and 155887/93).

It is clinically well known that the conventional antidepressant exhibits little effect in a single administration, and the effect is observed after at least about two weeks' consecutive administration.

With the conventional antidepressant, the enhancement of clonidine-induced aggressive behavior in mice is observed after at least ten days' consecutive administration [J. Neural Transmission, 52, 189 (1981)].

DISCLOSURE OF THE INVENTION

The present invention relates to an antidepressant containing as an active ingredient a triazine derivative, or a pharmaceutically acceptable salt thereof, the derivative being represented by the following Formula (I):

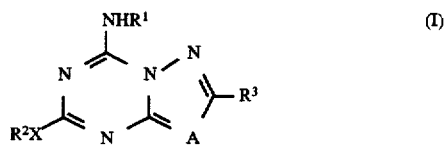

in which, $R^1$ represents hydrogen, substituted or unsubstituted lower alkyl, or substituted or unsubstituted lower alkanoyl; $R^2$ represents hydrogen, substituted or unsubstituted lower alkyl, substituted or unsubstituted lower alkenyl, substituted or unsubstituted cycloalkyl, substituted or unsubstituted aryl, substituted or unsubstituted aralkyl, or a substituted or unsubstituted heterocyclic group; $R^3$ represents a substituted or unsubstituted heterocyclic group; X represents a single bond, O, S, S(O), S(O)$_2$, or $NR^4$ (in which $R^4$ represents hydrogen, or substituted or unsubstituted lower alkyl; or $R^2$ and $NR^4$ are combined to form a substituted or unsubstituted 4 to 6-membered saturated heterocyclic group); and A represents N or $CR^5$ (in which $R^5$ represents hydrogen, or substituted or unsubstituted lower alkyl).

The present invention also relates to a method of treating depression comprising administration of an effective amount of a triazine derivative represented by the above formula (I) or a pharmaceutically acceptable salt thereof.

The present invention further relates to the use of a triazine derivative represented by the above formula (I) or a pharmaceutically acceptable salt thereof for the preparation of a pharmaceutical composition which is useful for treating depression.

The present invention further relates to the use of a triazine derivative represented by the above formula (I) or a pharmaceutically acceptable salt thereof for treating depression.

Furthermore, the present invention relates to a composition for treating depression comprising, in a pharmaceutically acceptable dosage form, an effective amount of a triazine derivative represented by the above formula (I) or a pharmaceutically acceptable salt thereof in association with a pharmaceutically acceptable carrier.

The compounds represented by Formula (I) are hereinafter referred to as Compound (I).

In the definitions of the groups in Formula (I), the lower alkyl means a straight-chain or branched alkyl group having 1 to 6 carbon atoms such as methyl, ethyl, propyl, isopropyl, butyl, isobutyl, sec-butyl, tert-butyl, pentyl, neopentyl, and hexyl. The lower alkanoyl means a straight-chain or branched alkanoyl group having 1 to 7 carbon atoms such as formyl, acetyl, propionyl, butyryl, isobutyryl, pivaloyl, and hexanoyl. The lower alkenyl means a straight-chain or branched alkenyl group having 2 to 6 carbon atoms such as vinyl, 1-methylvinyl, 1-propenyl, 2-propenyl, 1-butenyl, 2-methyl-1-propenyl, 1,3-butadienyl, 1-pentenyl, 4-pentenyl, 1-hexenyl, 1,4-hexadienyl, and 5-hexenyl. The cycloalkyl means a cycloalkyl group having 3 to 8 carbon atoms such as cyclopropyl, cyclobutyl, cyclopentyl, cyclohexyl, cycloheptyl, and cyclooctyl, a bicycloalkyl group having 7 to 12 carbon atoms such as norbornyl, or a tricycloalkyl group having 7 to 12 carbon atoms. Examples of the aryl are phenyl, naphthyl, indenyl, and anthryl. The aralkyl means an aralkyl group having 7 to 15 carbon atoms such as benzyl, 1-phenylethyl, 2-phenylethyl, 2-phenylpropyl, and diphenylmethyl. Examples of the heterocyclic group are furyl, thienyl, pyrrolyl, pyranyl, thiopyranyl, pyridyl, oxazolyl, thiazolyl, imidazolyl, pyrimidyl, triazinyl, indolyl, quinolyl, purinyl, benzoxazolyl, benzothiazolyl, and benzimidazolyl. Examples of the 4 to 6-membered saturated heterocyclic group are azetidino, pyrrolidino, morpholino, and thiomorpholino.

The substituted lower alkyl, the substituted lower alkanoyl, the substituted lower alkenyl, the substituted cycloalkyl, the substituted aryl, the substituted aralkyl, the substituted heterocyclic group, and the substituted 4 to 6-membered saturated heterocyclic group each has 1 to 3 independently-selected substituents. Examples of the substituents are lower alkyl, hydroxy, hydroxy-lower alkyl, halogeno-lower alkyl, lower alkoxy, lower alkoxycarbonyl, lower alkylthio, lower alkylsulfinyl, lower alkylsulfonyl, aryloxy, aralkyloxy, halogeno-aryloxy, halogeno-aralkyloxy, carboxy, carbamoyl, lower alkanoyl, aroyl, aryl, halogen, nitro, amino, cyano, and trifluoromethyl. The lower alkyl and the lower alkyl moiety of the hydroxy-lower alkyl, the halogeno-lower alkyl, the lower alkoxy, the lower alkoxycarbonyl, the lower alkylthio, the lower alkylsulfinyl, and the lower alkylsulfonyl have the same meaning as the lower alkyl defined above. The aryl and the aryl moiety of the aryloxy, the halogeno-aryloxy, and the aroyl have the same meaning as the aryl defined above. The aralkyl moiety of the aralkyloxy and the halogeno-aralkyloxy have the same meaning as the aralkyl defined above. The lower alkanoyl has the same meaning as the lower alkanoyl defined above. The halogen and the halogen moiety of the halogeno-lower alkyl, the halogeno-aryloxy, and the halogeno-aralkyloxy include fluorine, chlorine, bromine, and iodine.

The above-mentioned pharmaceutically acceptable salts of Compounds (I) include pharmaceutically acceptable acid addition salts, metal salts, ammonium salts, organic amine addition salts, and amino acid addition salts.

Examples of the pharmaceutically acceptable acid addition salts of Compounds (I) are inorganic acid addition salts such as hydrochloride, sulfate, and phosphate, and organic acid addition salts such as acetate, maleate, fumarate, tartrate, and citrate. Examples of the pharmaceutically acceptable metal salts are alkali metal salts such as sodium salt and potassium salt, alkaline earth metal salts such as magnesium salt and calcium salt, aluminium salt, and zinc salt. Examples of the pharmaceutically acceptable ammonium salts are ammonium salt and tetramethyl ammonium salt. Examples of the pharmaceutically acceptable organic amine addition salts are salts with morpholine and piperidine. Examples of the pharmaceutically acceptable amino acid addition salts are salts with lysine, glycine, and phenylalanine.

Compounds (I) including novel compounds can be produced according to the methods disclosed in the above-described literatures or similar methods thereto.

The desired compounds in the processes can be isolated and purified by purification methods conventionally used in organic synthetic chemistry, for example, filtration, extraction, washing, drying, concentration, recrystallization, and various kinds of chromatography.

In the case where a salt of Compound (I) is desired and it is produced in the form of the desired salt, it can be subjected to purification as such. In the case where Compound (I) is produced in the free state and its salt is desired, Compound (I) is dissolved or suspended in a suitable solvent, followed by addition of an acid or a base to form a salt.

Compounds (I) and pharmaceutically acceptable salts thereof may be in the form of adducts with water or various solvents, which can also be used as the therapeutic agents of the present invention.

Some of Compounds (I) can exist in the form of stereoisomers and optical isomers, and all possible stereoisomers, optical isomers, and mixtures thereof can also be used as the therapeutic agents of the present invention.

Examples of Compound (I) are shown in Table 1.

TABLE 1

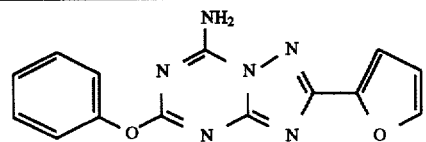

(Compound 1)

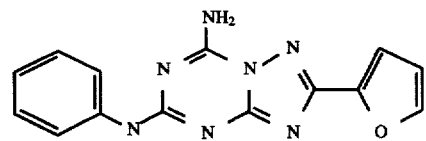

(Compound 2)

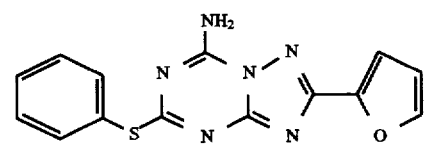

(Compound 3)

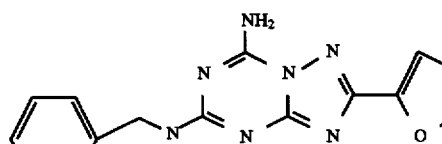

(Compound 4)

Compound 1

7-Amino-2-(2-furyl)-5-phenoxy[1,2,4]triazolo[1,5-a]-1,3,5-triazine (compound disclosed in Example 1 of Japanese Published Unexamined Patent Application No. 97855/93)

Melting Point: 250.7°–251.7° C.

Elemental Analysis: $C_{14}H_{10}N_6O_2$ Calcd. (%): C, 57.14; H, 3.43; N, 28.56 Found (%): C, 56.89; H, 3.36; N, 28.35

NMR (DMSO-$d_6$) δ(ppm): 9.00(2H, brs), 7.92(1H, d, J=1.5 Hz), 7.49–7.43(2H, m), 7.28–7.23(3H, m), 7.12 (1H, d, J=3.0 Hz), 6.70(1H, dd, J=1.5, 3.0 Hz)

Compound 2

7-Amino-5-anilino-2-(2-furyl)[1,2,4]triazolo[1,5-a]-1,3,5-triazine (compound disclosed in Example 27 of Japanese Published Unexamined Patent Application No. 97855/93)

Melting Point: >280° C.

Elemental Analysis: $C_{14}H_{11}N_7O·0.1C_2H_5OH$ Calcd. (%): C, 57.25; H, 3.92; N, 32.91 Found (%): C, 57.01; H, 3.73; N, 32.77

NMR (DMSO-d$_6$) δ(ppm): 9.68(1H, s), 8.44(2H, brs), 7.90(1H, d, J=1.7 Hz), 7.80(2H, d, J=8.3 Hz), 7.31 (2H, dd, J=7.3, 8.3 Hz), 7.12(1H, d, J=3.3 Hz), 7.00 (1H, t, J=7.3 Hz), 6.70(1H, dd, J=1.7, 3.3 Hz)

Compound 3

7-Amino-2-(2-furyl)-5-phenylthio[1,2,4]triazolo[1,5-a]-1,3,5-triazine (compound disclosed in Example 2 of Japanese Published Unexamined Patent Application No. 97855/93)

Melting Point: >280° C.

Elemental Analysis: $C_{14}H_{10}N_6OS \cdot 0.1H_2O$ Calcd. (%): C, 53.87; H, 3.29; N, 26.92 Found (%): C, 53.76; H, 3.21; N, 26.88

NMR (DMSO-d$_6$) δ(ppm): 8.94(2H, brs), 7.91(1H, d, J=1.7 Hz), 7.64(2H, dd, J=2.0, 5.3 Hz), 7.51–7.50(3H, m), 7.12(1H, d, J=3.3 Hz), 6.70(1H, dd, J=1.7, 3.3 Hz)

Compound 4

7-Amino-5-benzylamino-2-(2-furyl)[1,2,4]triazolo[1,5-a]-1,3,5-triazine (compound disclosed in Example 31 of Japanese Published Unexamined Patent Application No. 97855/93)

Melting Point: 223.6°–225.0° C.

Elemental Analysis: $C_{15}H_{13}N_7O$ Calcd. (%): C, 58.63; H, 4.26; N, 31.90 Found (%): C, 58.71; H, 4.19; N, 32.07

NMR (DMSO-d$_6$) δ(ppm): 8.19(2H, brs), 7.97(1H, t, J=5.9 Hz), 7.86(1H, d, J=1.7 Hz), 7.33–7.22(5H, m), 7.03 (1H, d, J=3.3 Hz), 6.67(1H, dd, J=1.7, 3.3 Hz), 4.50(2H, d, J=5.9 Hz)

The pharmacological activities of Compound (I) are shown below by experimental examples.

Experimental Example 1

Effect on Clonidine-Induced Aggressive Behavior

The effect of a test compound on the aggressive behavior induced by intraperitoneal administration of clonidine was investigated [Eur. J. Pharmacol., 29, 374 (1968)].

The experiment was carried out by using several groups of ddy-strain male mice (weighing 20 to 25 g, Japan SLC), each group consisting of two mice. The test compound was suspended in injectable distilled water (Otsuka Pharmaceutical Co., Ltd.) containing Tween 80 [polyoxyethylene (20) sorbitan monooleate]. Clonidine hydrochloride (Sigma Co.) was dissolved in physiological saline solution (Otsuka Pharmaceutical Co., Ltd.). The test compound suspension or the suspension containing no test compound (control) was orally administered to separate groups of the mice (0.1 ml per 10 g of body weight). Sixty minutes after the oral administration of the test compound, clonidine hydrochloride (20 mg/kg) was intraperitoneally injected. The number of biting attacks during 30 minutes after clonidine treatment was counted. The effect of the compound was evaluated by comparing the average number of biting attacks of the test compound-administered groups with that of control groups (Statistical comparison: Student's t-test).

The results are shown in Table 2.

TABLE 2

| Test Compd. | Dose (mg/kg, po) | Number of the Biting Attacks (Counts: mean ± S.E.M.) | | Number of the Attacks of Test Compound-Treated Group/ Number of the Attacks of Control Group |
|---|---|---|---|---|
| | | Control Group (number of animals) | Test Compound-Treated Group (number of animals) | |
| 1 | 10 | 11.9 ± 2.60 (15) | 48.5 ± 12.34* (15) | 4.1 |
| 1 | 2.5 | 11.9 ± 2.60 (15) | 55.2 ± 12.02** (15) | 4.6 |
| 2 | 10 | 1.67 ± 1.17 (15) | 22.40 ± 8.22* (15) | 13.4 |
| 3 | 2.5 | 2.47 ± 1.40 (15) | 10.73 ± 2.41** (15) | 4.3 |
| 4 | 10 | 2.40 ± 1.45 (10) | 37.30 ± 9.90** (10) | 15.5 |

*: $p < 0.05$;
**: $p < 0.01$

Compound (I) and pharmaceutically acceptable salts thereof exhibit activity in enhancement of clonidine-induced aggressive behavior, and are useful as an antidepressant.

EXPERIMENTAL EXAMPLE 2

Effect on Reserpine-Induced Hypo-Mobility

The experiment was carried out by using several groups of ddy-strain male mice (weighing 21 to 30 g, Japan SLC), each group consisting of 8 mice. Reserpine (Apopron injection 1 mg, Daiichi Seiyaku Co., Ltd.) dissolved in injectable distilled water (Otsuka Pharmaceutical Co., Ltd.) was intraperitoneally administered to each mouse at a dose of 5 mg/kg. The test compound was orally administered to separate groups of the mice after 18 to 24 hours of the reserpine administration. The amount of active movements of each mouse was measured by using Automex-II (Columbus Instruments International Corp.) for the period of 30 minutes starting 60 minutes after the administration of the test compound. The effect of the compounds was evaluated by comparing the average counts of the active movements of the test compound-administered groups with those of the control groups. Statistical comparison of the values was carried out by Williams-Wilcoxon test.

The results are shown in Table 3.

TABLE 3

| Group | Administration | | Dose of Test Compound (mg/kg) | Amount of Active Movements (Counts; mean ± S.E.M) |
|---|---|---|---|---|
| Normal Control | Reserpine | (−) | | |
| | Test Compound | (−) | — | 1558 ± 186.9 |
| Reserpine | Reserpine | (+) | | |
| | Test Compound | (−) | — | 8 ± 3.6 |
| Compound 1 | Reserpine | (+) | | |
| | Compound 1 | (+) | 10 | 493 ± 111.6** |
| Normal Control | Reserpine | (−) | | |
| | Test Compound | (−) | — | 1284 ± 95.5 |
| Reserpine | Reserpine | (+) | | |
| | Test Compound | (−) | — | 87 ± 50.9 |
| Compound 2 | Reserpine | (+) | | |
| | Compound 2 | (+) | 10 | 190 ± 70.0 |
| Compound 3 | Reserpine | (+) | | |
| | Compound 3 | (+) | 10 | 410 ± 162.2* |
| Compound 4 | Reserpine | (+) | | |
| | Compound 4 | (+) | 10 | 470 ± 79.0** |

*: $p < 0.05$;
**: $p < 0.01$ (comparison with Reserpine-treated group)

EXPERIMENTAL EXAMPLE 3

Forced Swimming Test (Measurement of Immobility Time)

The experiment was carried out by using several groups of ddY-strain male mice (weighing 21 to 26 g, Japan SLC), each group consisting of 10 mice. The animals were housed in the animal quarters with free access to food and water until experimental use. Meanwhile, room temperature and relative humidity were kept at 23°±1° C. and 55±5%, respectively. The animals showing an abnormal response in spontaneous activity, muscle tone, and visual placing were excluded in advance. Test compounds were suspended in 0.3% Tween 80 and orally administered to the animals one hour prior to the test. Only 0.3% Tween 80 at 10 mg/kg were orally administered to control groups. The measurement of immobility time was carried out according to the procedure of Porsolt et al. [(Arch. int. Pharmacodyn. Ther., 229, 327 (1977)]. The mouse was kept swimming for 6 minutes in a cylindrical tank made of transparent acrylic resin (diameter: 10 cm; height: 25 cm) containing 9 cm of water at 23°±1° C. Although the mouse swims and struggles for escaping from the tank immediately after entering the tank, its movement gradually decreases in one or two minutes. The measurement of immobility time was carried out by counting, by seconds, the time during which the mouse did not make any attempt to escape (immobility time: behavioral despair) for the last 4 minutes (240 seconds). For the first 2 minutes, immobility time was not measured. In order to reduce an influence of a circadian rhythm on the animals, 5 mice of each group were tested in the morning, and another 5 mice of each group were tested in the afternoon. The measurement of immobility time was carried out simultaneously with two animals and by blind test to observers as to the presence or absence of the test compound and the distinction in the amount of the test compound. Statistical analysis of the results was carried out with a one-way analysis of variance by Steel-test for comparisons between the control group treated with only a solvent and the test compound-treated group.

The results are shown in Table 4.

TABLE 4

| Test Compd. | Dose (mg/kg, po) | Immobility Time (Seconds: mean ± S.E.M.) | |
|---|---|---|---|
| | | Control Group (number of animals) | Test Compound-Treated Group (number of animals) |
| 1 | 2.5 | 125.2 ± 17.7 (10) | 66.1 ± 15.4 (10) |
| 2 | 2.5 | 152.7 ± 16.0 (10) | 88.6 ± 22.5 (10) |

EXPERIMENTAL EXAMPLE 4

Acute Toxicity Test

Test compounds were orally administered to groups of dd-strain male mice weighing 20±1 g, each group consisting of three mice. Seven days after the administration, minimum lethal dose (MLD) of each compound was determined by observing the mortality.

The MLD value of Compound 1 is greater than 300 mg/kg, indicating that the toxicity of the compound is weak. Therefore, the compound can be safely used in a wide range of doses.

Compound (I) and pharmaceutically acceptable salts thereof can be administered as they are, or in the form of various pharmaceutical compositions. The pharmaceutical compositions in accordance with the present invention can be prepared by uniformly mixing an effective amount of Compound (I) or a pharmaceutically acceptable salt thereof, as an active ingredient, with a pharmaceutically acceptable carrier. It is desired that such pharmaceutical compositions are prepared in a unit dose form suitable for oral administration or administration through injection.

For preparing a pharmaceutical composition for oral administration, any useful pharmaceutically acceptable carrier can be used. For example, liquid preparations for oral administration such as suspension and syrup can be prepared using water, sugars such as sucrose, sorbitol, and fructose, glycols such as polyethylene glycol and propylene glycol, oils such as sesame oil, olive oil, and soybean oil, preservatives such as p-hydroxybenzoates, flavors such as strawberry flavor and peppermint, and the like. Powders, pills, capsules, and tablets can be prepared using excipients such as lactose, glucose, sucrose, and mannitol, disintegrating agents such as starch and sodium alginate, lubricants such as magnesium stearate and talc, binders such as polyvinyl alcohol, hydroxypropyl cellulose, and gelatin, surfactants such as fatty acid esters, plasticizers such as glycerin, and the like. Tablets and capsules are the most useful oral unit dose forms because of the readiness of administration. For preparing tablets and capsules, solid pharmaceutical carriers are used.

Injectable preparations can be prepared using a carrier such as distilled water, a salt solution, a glucose solution, or a mixture of a salt solution and a glucose solution. The preparations can be prepared in the form of solution, suspension or dispersion according to a conventional method by using a suitable solubilizing auxiliary or suspending agent.

Compound (I) and pharmaceutically acceptable salts thereof can be administered orally or parenterally as injections in the said dosage forms. The effective dose and the administration schedule vary depending upon the mode of administration, the age, body weight, and conditions of a patient, etc. However, generally, Compound (I) or a pharmaceutically acceptable salt thereof is administered in a daily dose of 1 to 50 mg/kg in 3 to 4 parts.

Certain embodiments of the invention are illustrated in the following examples.

BEST MODE FOR CARRYING OUT THE INVENTION

Example 1

Tablets

Tablets having the following composition were prepared in a conventional manner.

Compound 1 (40 g) was mixed with 286.8 g of lactose and 60 g of potato starch, followed by addition of 120 g of a 10% aqueous solution of hydroxypropylcellulose. The resultant mixture was kneaded, granulated, and then dried by a conventional method. The granules were refined to give granules used to make tablets. After mixing the granules with 1.2 g of magnesium stearate, the mixture was formed into tablets each containing 20 mg of the active ingredient by using a tablet maker (Model RT-15, Kikusui) having pestles of 8 mm diameter.

| Composition of One Tablet | |
|---|---|
| Compound 1 | 20 mg |
| Lactose | 143.4 mg |
| Potato Starch | 30 mg |
| Hydroxypropylcellulose | 6 mg |
| Magnesium Stearate | 0.6 mg |
| | 200 mg |

EXAMPLE 2

Fine Granules

Fine granules having the following composition were prepared in a conventional manner.

Compound 1 (20 g) was mixed with 655 g of lactose and 285 g of corn starch, followed by addition of 400 g of a 10% aqueous solution of hydroxypropylcellulose. The resultant mixture was kneaded, granulated, and then dried by a conventional method to give fine granules containing 20 g of the active ingredient in 1,000 g.

| Composition of One Pack of Fine Granules | |
|---|---|
| Compound 1 | 20 mg |
| Lactose | 655 mg |
| Corn Starch | 285 mg |
| Hydroxypropylcellulose | 40 mg |
| | 1,000 mg |

EXAMPLE 3

Capsules

Capsules having the following composition were prepared in a conventional manner.

Compound 1 (200 g) was mixed with 995 g of Avicel and 5 g of magnesium stearate. The mixture was put in hard capsules No. 4 each having a capacity of 120 mg by using a capsule filler (Model LZ-64, Zanashi) to give capsules each containing 20 mg of the active ingredient.

| Composition of One Capsule | |
|---|---|
| Compound 1 | 20 mg |
| Avicel | 99.5 mg |
| Magnesium Stearate | 0.5 mg |
| | 120 mg |

EXAMPLE 4

Injections

Injections having the following composition were prepared in a conventional manner.

Compound 1 (1 g) was dissolved in 100 g of purified soybean oil, followed by addition of 12 g of purified egg yolk lecithin and 25 g of glycerine for injection. The resultant mixture was made up to 1,000 ml with distilled water for injection, thoroughly mixed, and emulsified by a conventional method. The resultant dispersion was subjected to aseptic filtration by using 0.2 μm disposable membrane filters, and then aseptically put into glass vials in 2 ml portions to give injections containing 2 mg of the active ingredient per vial.

| Composition of One Injection Vial | |
|---|---|
| Compound 1 | 2 mg |
| Purified Soybean Oil | 200 mg |
| Purified Egg Yolk Lecithin | 24 mg |
| Glycerine for Injection | 50 mg |
| Distilled Water for Injection | 1.72 ml |
| | 2.00 ml |

EXAMPLE 5

Tablets

Tablets having the following composition were prepared in a conventional manner.

Compound 2 (40 g) was mixed with 286.8 g of lactose and 60 g of potato starch, followed by addition of 120 g of a 10% aqueous solution of hydroxypropylcellulose. The resultant mixture was kneaded, granulated, and then dried by a conventional method. The granules were refined to give granules used to make tablets. After mixing the granules with 1.2 g of magnesium stearate, the mixture was formed into tablets each containing 20 mg of the active ingredient by using a tablet maker (Model RT-15, Kikusui) having pestles of 8 mm diameter.

| Composition of One Tablet | |
|---|---|
| Compound 2 | 20 mg |
| Lactose | 143.4 mg |
| Potato Starch | 30 mg |
| Hydroxypropylcellulose | 6 mg |
| Magnesium Stearate | 0.6 mg |
| | 200 mg |

EXAMPLE 6

Tablets

Tablets having the following composition were prepared in a conventional manner.

Compound 3 (40 g) was mixed with 286.8 g of lactose and 60 g of potato starch, followed by addition of 120 g of a 10% aqueous solution of hydroxypropylcellulose. The resultant mixture was kneaded, granulated, and then dried by a conventional method. The granules were refined to give granules used to make tablets. After mixing the granules with 1.2 g of magnesium stearate, the mixture was formed into tablets each containing 20 mg of the active ingredient by using a tablet maker (Model RT-15, Kikusui) having pestles of 8 mm diameter.

| Composition of One Tablet | |
|---|---|
| Compound 3 | 20 mg |
| Lactose | 143.4 mg |
| Potato Starch | 30 mg |
| Hydroxypropylcellulose | 6 mg |
| Magnesium Stearate | 0.6 mg |
| | 200 mg |

INDUSTRIAL APPLICABILITY

According to the present invention, there can be provided an excellent antidepressant.

We claim:

1. A method of treating depression comprising administration of an effective amount of a triazine derivative of the formula:

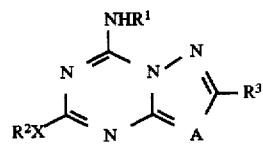

in which $R^1$ represents hydrogen, substituted or unsubstituted lower alkyl, or substituted or unsubstituted lower alkanoyl; $R^2$ represents hydrogen, substituted or unsubstituted lower alkyl, substituted or unsubstituted lower alkenyl, substituted or unsubstituted cycloalkyl, substituted or unsubstituted aryl, substituted or unsubstituted aralkyl, or substituted or unsubstituted heterocyclic group; $R^3$ represents a substituted or unsubstituted heterocyclic group; X represents a single bond, O, S, S(O), $S(O)_2$, or $NR^4$ (in which $R^4$ represents hydrogen, or substituted or unsubstituted lower alkyl; or $R^2$ and $NR^4$ are combined to form a substituted or unsubstituted 4 to 6-membered saturated heterocyclic group); and A represents N or $CR^5$ (in which $R^5$ represents hydrogen, or substituted or unsubstituted lower alkyl), or a pharmaceutically acceptable salt thereof.

* * * * *

UNITED STATES PATENT AND TRADEMARK OFFICE
CERTIFICATE OF CORRECTION

PATENT NO. : 5,789,407

DATED : August 4, 1998

INVENTOR(S): FUMIO SUZUKI ET AL.

It is certified that error appears in the above-identified patent and that said Letters Patent is hereby corrected as shown below:

Title page, item
[56] REFERENCES CITED

Foreign Patent Documents
    Insert: --515107  11/92  European Pat. Off.--.

[75] INVENTORS

"Shunji Ichikawa;" should read --Shunji Ichikawa,
        Tata-gun, Japan;--; and "both of" should be deleted.

COLUMN 5

Line 64, "ddy-strain" should read --ddY-strain--.

COLUMN 6

Line 50, "ddy-strain" should read --ddY-strain--.

Signed and Sealed this

Twenty-first Day of September, 1999

Attest:

Q. TODD DICKINSON

*Attesting Officer*    *Acting Commissioner of Patents and Trademarks*